(12) United States Patent
Okada

(10) Patent No.: US 11,109,748 B2
(45) Date of Patent: Sep. 7, 2021

(54) MEDICAL OBSERVATION APPARATUS

(71) Applicant: Sony Olympus Medical Solutions Inc., Tokyo (JP)

(72) Inventor: Naobumi Okada, Saitama (JP)

(73) Assignee: SONY OLYMPUS MEDICAL SOLUTIONS INC., Tokyo (JP)

(*) Notice: Subject to any disclaimer, the term of this patent is extended or adjusted under 35 U.S.C. 154(b) by 0 days.

(21) Appl. No.: 16/734,432

(22) Filed: Jan. 6, 2020

(65) Prior Publication Data
US 2020/0297200 A1   Sep. 24, 2020

(30) Foreign Application Priority Data
Mar. 18, 2019 (JP) .............................. JP2019-050434

(51) Int. Cl.
| | | |
|---|---|---|
| A61B 1/045 | (2006.01) | |
| A61B 1/05 | (2006.01) | |
| A61B 1/06 | (2006.01) | |
| H04N 5/232 | (2006.01) | |
| A61B 1/04 | (2006.01) | |
| A61B 1/00 | (2006.01) | |

(52) U.S. Cl.
CPC .......... *A61B 1/045* (2013.01); *A61B 1/00133* (2013.01); *A61B 1/00188* (2013.01); *A61B 1/043* (2013.01); *A61B 1/05* (2013.01); *A61B 1/0676* (2013.01); *H04N 5/23296* (2013.01); *H04N 5/23299* (2018.08)

(58) Field of Classification Search
None
See application file for complete search history.

(56) References Cited

U.S. PATENT DOCUMENTS

| | | | | |
|---|---|---|---|---|
| 2007/0265502 | A1* | 11/2007 | Minosawa | ......... A61B 17/3421 600/173 |
| 2009/0080186 | A1* | 3/2009 | Helmreich | ........... G02B 6/0073 362/231 |
| 2015/0018690 | A1* | 1/2015 | Kang | ..................... A61B 5/418 600/473 |
| 2015/0220240 | A1* | 8/2015 | Tsukijishin | ............ A61B 90/37 348/77 |
| 2020/0188049 | A1* | 6/2020 | Chang | .................... A61B 34/35 |

FOREIGN PATENT DOCUMENTS

WO   2016/017532 A1   2/2016

* cited by examiner

*Primary Examiner* — Eileen M Adams
(74) *Attorney, Agent, or Firm* — Xsensus LLP

(57) ABSTRACT

A medical observation apparatus includes: a camera configured to capture an observation object to output an imaging signal; a support configured to movably support the camera; and controller circuitry configured to control, when a normal observation mode with white light is switched to a special-light observation mode with special light, the support such that the camera is moved to a position so as to obtain a working distance that is set for the special-light observation mode and that is shorter than a working distance in the normal observation mode.

9 Claims, 10 Drawing Sheets

MEDICAL OBSERVATION APPARATUS

This application claims priority from Japanese Application No. 2019-050434, filed on Mar. 18, 2019, the contents of which are incorporated by reference herein in its entirety.

BACKGROUND

The present disclosure relates to a medical observation apparatus to observe a micro site of an observation object.

As a medical observation system to observe a micro site in the brain, the heart, or the like, of the patient, who is an observation object, during the surgery on the micro site, there is a known optical microscope system that includes a microscope unit including an optical magnifying system and an imaging element to enlarge the micro site (for example, see International Publication Pamphlet No. 2016/017532).

In recent years, there has been a disclosure of an observation method for executing the special light observation using special light other than the normal observation using white light. Specifically, the special light observation includes the technology called NBI (narrow band imaging), the technology called IRI (infra-red imaging), the technology called AFI (auto fluorescence imaging), and the technology called PDD (photodynamic diagnosis).

In the NBI, the illumination light with a narrow band having a wavelength of 415 nm and 540 nm as its center wavelength is emitted and, by the use of an absorption difference in the light at each wavelength with regard to hemoglobin, the states of blood vessels in the superficial layer of the mucous membrane and a deeper layer are observed. The light of 415 nm is absorbed by hemoglobin in the superficial layer of the mucous membrane, and the light of 540 nm is absorbed by hemoglobin in a slightly deeper layer.

In the IRI, the medical agent called indocyanine green (ICG) whose absorption peak is in the near-infrared light having a wavelength of approximately 805 nm in blood is intravenously injected as a contrast agent, the excitation light having a center wavelength of approximately 805 nm is emitted, and the fluorescence from the ICG is observed so that the presence or absence of a blood flow is diagnosed.

In the AFI, a fluorescence agent is previously administered into the subject, a fluorescence image generated from the subject due to the emission of excitation light is observed, and the presence or absence or the shape of the fluorescence image is observed so that a tumor is diagnosed. In the normal tissue, fluorescence from the fluorescence agent is generated in the superficial layer of the mucous membrane, and fluorescence from the fluorescent material is significantly decreased due to the blood vessel accumulation or the mucosal thickening in the superficial layer of the mucous membrane of the lesion.

In the PDD, an image is obtained, which easily distinguishes between a cancer cell and a normal cell by the use of the characteristics such that, when the solvent of aminolaevulinic acid (5-ALA) is administered into the patient, it is metabolized to a blood ingredient (heme) in the normal tissue of the body but, in a cancer cell, is stored as a substance called PpIX as an intermediate instead of being metabolized, and when PpIX is irradiated with blue light (a center wavelength of 410 nm), fluorescence is emitted in red (a peak wavelength of 630 nm). A normal cell generates blue light when it receives the emitted blue light, e.g., the light of 460 nm at the edge of the emitted blue light.

SUMMARY

In the special light observation, generally, there is a small amount of light detectable by a microscope unit as compared with that in the normal observation. For example, the amount of illumination light is small in the NBI, and the amount of fluorescence generated by an observed region is small with respect to excitation light in the AFI. When the amount of light detected by the microscope unit is small, the ratio (S/N) of a detection signal of an imaging element with respect to noise is degraded, and the quality of the generated image is decreased.

According to one aspect of the present disclosure, there is provided a medical observation apparatus including: a camera configured to capture an observation object to output an imaging signal; a support configured to movably support the camera; and controller circuitry configured to control, when a normal observation mode with white light is switched to a special-light observation mode with special light, the support such that the camera is moved to a position so as to obtain a working distance that is set for the special-light observation mode and that is shorter than a working distance in the normal observation mode.

DETAILED DESCRIPTION

With reference to the accompanying drawings, configurations (hereinafter also referred to as "embodiments") for implementing the present disclosure are described below. The drawings are merely schematic, and the drawings may include parts that are different in the dimension relationship or the proportion from each other.

First Embodiment

Figure 1:
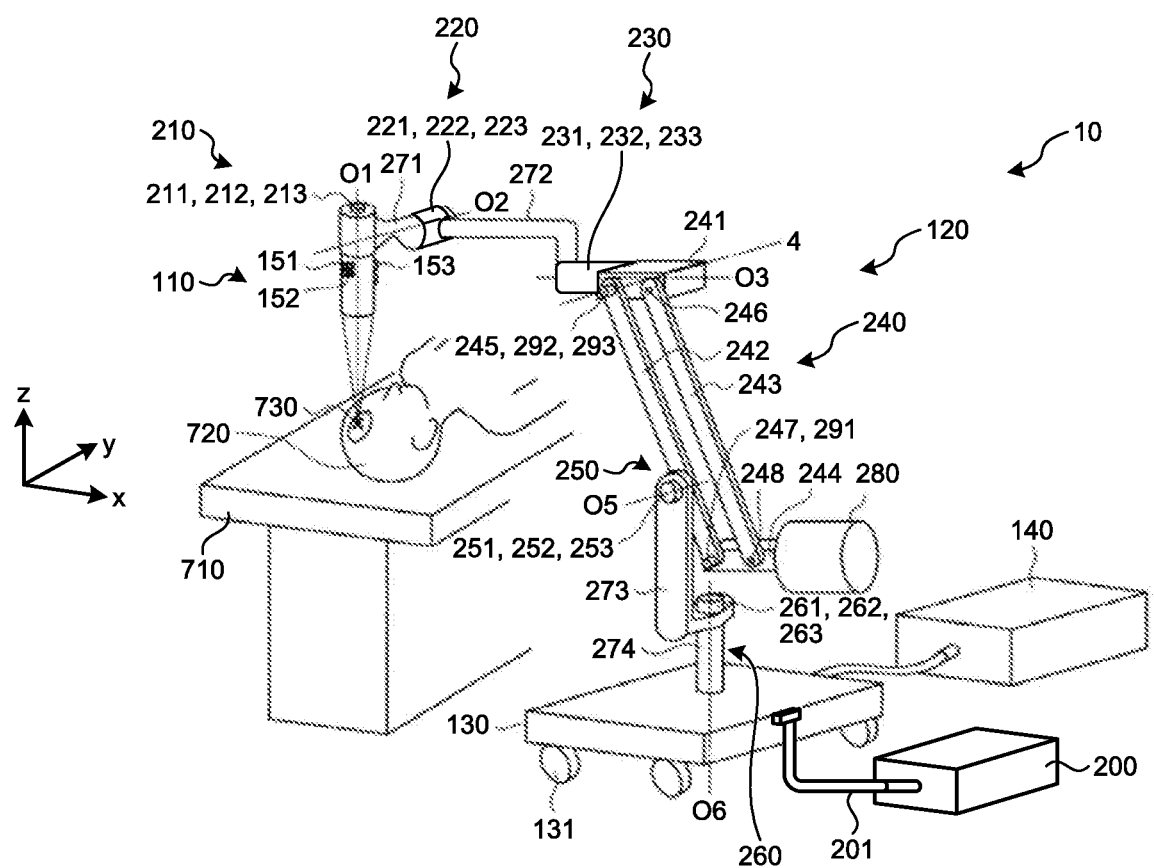
FIG. 1 is a perspective view that illustrates an external configuration of a medical observation apparatus according to a first embodiment.
Figure 2:
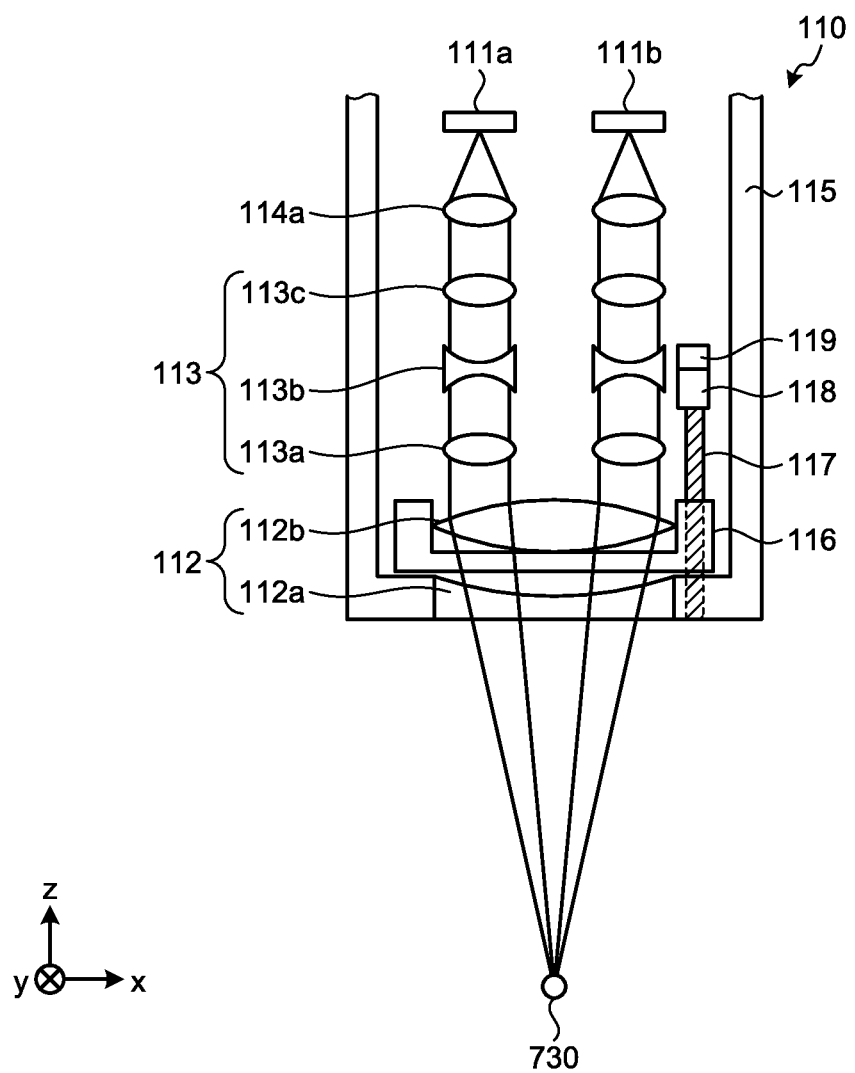
FIG. 2 is a partially enlarged cross-sectional view that illustrates configurations of a microscope unit and its periphery in the medical observation apparatus according to the first embodiment.

FIG. 1 is a diagram that illustrates a configuration of a medical observation apparatus according to a first embodiment. FIG. 2 is a partially enlarged cross-sectional view that illustrates configurations of a microscope unit and its periphery in the medical observation apparatus according to the first embodiment.

A medical observation apparatus 10 includes: an imaging unit 110 that captures a surgery site of the patient that is an observation object; a supporting unit 120 (arm unit 120) that supports the imaging unit 110; a base 130 (fundamental part 130) that is coupled to one end of the supporting unit 120 to support the imaging unit 110 and the supporting unit 120; and a controller 140 that controls the operation of the medical observation apparatus 10. The medical observation apparatus 10 is coupled to a light source device 200 that supplies illumination light to the imaging unit 110 via a light guide 201 including an optical fiber, or the like. FIG. 2 illustrates a state where the imaging unit 110 of the medical observation apparatus 10 captures a surgery site 730 (observation point 730) of a patient 720 lying on a surgery bed 710. Hereinafter, for descriptive purposes, the user who performs various types of operations on the medical observation apparatus 10 is referred to as an operator. This description, however, does not limit the user who uses the medical observation apparatus 10, and any user such as other medical staff may perform various operations on the medical observation apparatus 10.

The base 130 supports the imaging unit 110 and the supporting unit 120. The base 130 has a plate-like shape, and the top surface thereof is coupled to one end of the supporting unit 120. In the medical observation apparatus 10, the imaging unit 110 is coupled to the other end (the distal end) of the supporting unit 120 extending from the base 130. The lower surface of the base 130 is provided with multiple casters 131 so that the medical observation apparatus 10 is in contact with the floor surface via the casters 131. The medical observation apparatus 10 is configured to move on the floor surface with the casters 131.

In the following description, the direction perpendicular to the floor surface where the medical observation apparatus 10 is placed is defined as the z-axis direction. Two directions perpendicular to the z-axis direction are defined as the x-axis direction and the y-axis direction, respectively. In the illustrated example, the optical axis direction of the imaging unit 110 substantially matches the z-axis direction.

The controller 140 includes, for example, a processor, such as a CPU (central processing unit) or a DSP (digital signal processor), or a microcomputer having the processor installed therein, and performs arithmetic processing in accordance with a predetermined program to control the operation of the medical observation apparatus 10. For example, according to the first embodiment, the controller 140 sets any one of observation modes (the normal observation mode with white light and the special-light observation mode with special light). The controller 140 may switch the observation mode in response to the operator's operation input.

As the special-light observation mode, any one of the following is set: the NBI in which the illumination light with a narrow band having a wavelength of 415 nm and 540 nm as its center wavelength is emitted and, by the use of an absorption difference in the light at each wavelength with regard to hemoglobin, the states of blood vessels in the superficial layer of the mucous membrane and a deeper layer are observed; the IRI in which the medical agent called indocyanine green (ICG) whose absorption peak is in the near-infrared light having a wavelength of approximately 805 nm in blood is intravenously injected as a contrast agent, the excitation light having a center wavelength of approximately 805 nm is emitted, and the fluorescence from the ICG is observed so that the presence or absence of a blood flow is diagnosed; the AFI in which a fluorescence agent is previously administered into the subject, a fluorescence image generated from the subject due to the emission of excitation light is observed, and the presence or absence or the shape of the fluorescence image is observed so that a tumor is diagnosed; and the PDD that obtains an image that easily distinguishes between a cancer cell and a normal cell by the use of the characteristics such that, when the solvent of aminolaevulinic acid (5-ALA) is administered into the patient, it is metabolized to a blood ingredient (heme) in the normal tissue of the body but, in a cancer cell, is stored as a substance called PpIX as an intermediate instead of being metabolized, and when PpIX is irradiated with blue light (a center wavelength of 410 nm), fluorescence is emitted in red (a peak wavelength of 630 nm).

According to the first embodiment, white light is output from the light source device 200 in the normal observation mode, and the light having the wavelength corresponding to the set observation mode is output from the light source device 200 in the special-light observation mode.

The controller 140 controls the driving of an active axis during the switching of the above-described observation mode. Specifically, the controller 140 may calculate the distance from the imaging unit 110 to the observation point 730 based on the information about the focal length in the imaging unit 110. At the rotation axes of the supporting unit 120, encoders (encoders 212, 222, 232, 252, 262, and 292 described later) are provided to detect the rotation angles at the corresponding rotation axes so that the controller 140 may calculate the three-dimensional position and posture of the imaging unit 110 based on detection values of the encoders. Based on the calculated distance from the imaging unit 110 to the observation point 730 and the three-dimensional position and posture of the imaging unit 110, the controller 140 controls the driving of the actuator provided in an active axis such that the observation point 730 for the imaging unit 110 after the movement matches the observation point 730 for the imaging unit 110 before the movement.

The modes set by the controller 140 include operation modes (a fixed mode and an all-free mode) of the supporting unit 120.

The fixed mode is an operation mode in which the rotation at each of the rotation axes provided in the supporting unit 120 is restricted by a brake so that the position and the posture of the imaging unit 110 are fixed.

The all-free mode is an operation mode in which the brake is canceled so that the rotation at each of the rotation axes provided in the supporting unit 120 is allowed to be free and the position and the posture of the imaging unit 110 are adjustable due to the direct manual operation of the operator. The direct operation refers to the operation to move the imaging unit 110, for example, with the operator's hand touching the imaging unit 110.

A function of the controller 140 is described later in detail.

The imaging unit 110 is, for example, a microscope to capture a surgery site of the patient. The imaging unit 110 is configured to transmit captured image information to a display device such as a display panel or the like. The operator observes a surgery site while viewing the image captured by the imaging unit 110 and displayed on the display device and gives various types of treatments to the surgery site.

The imaging unit 110 includes a zoom switch 151 (zoom SW 151) and a focus switch 152 (focus SW 152) to adjust the capturing condition of the imaging unit 110 and an all-free switch 153 (all-free SW 153) to change the operation mode of the supporting unit 120. The operator may operate the zoom SW 151 and the focus SW 152 to adjust the magnification and the focal length, respectively, of the imaging unit 110. The magnification and the focal length of the imaging unit 110 may be adjusted under the control of the controller 140.

The operator may operate the all-free SW 153 to switch the operation mode of the supporting unit 120 to any one of the fixed mode and the all-free mode.

These switches do not necessarily need to be provided in the imaging unit 110. According to the first embodiment, it is appropriate as long as a system that has the functionality equivalent to those of the switches and that receives operation inputs is provided in the medical observation apparatus 10, and the specific configuration of the system is not limited. For example, these switches may be provided in a different part of the medical observation apparatus 10. Instructions to these switches may be remotely input to the medical observation apparatus 10 by using an input device such as a remote controller.

Although not illustrated in FIG. 2 to prevent the complexity of the drawing, a partial area of the imaging unit 110 may be provided with a grip part that is grasped by the operator. The operator grasps the grip part with the hand so as to manually move the imaging unit 110 in parallel and at a tilt. According to the first embodiment, the operator operates the all-free SW 153 while grasping the grip part. Therefore, it is preferable that the location positions of the grip part and the all-free SW 153 are determined in consideration of the positional relationship between them and the operability for the operator.

The configuration of the imaging unit 110 is described with reference to FIG. 2. FIG. 2 is a cross-sectional view of the imaging unit 110 on the plane that passes through the optical axis and is parallel to the optical axis. A pair of imaging elements 111a and 111b, which is compatible with what is called a stereo camera, is provided inside a casing 115 of the imaging unit 110. Various known imaging elements, such as a CCD (charge coupled device) sensor or a CMOS (complementary metal oxide semiconductor) sensor, may be used as the imaging elements 111a and 111b. Information on an image captured by the imaging elements 111a and 111b is transmitted to a display device installed in a surgery room so that the display device presents the captured image of a surgery site.

An objective optical system 112 including a pair of a concave lens 112a and a convex lens 112b, a variable-power optical system 113 including a convex lens 113a, a concave lens 113b, and a convex lens 113c, and a focusing optical system including a convex lens 114a are provided prior to the imaging elements 111a and 111b. The convex lens 113a, the concave lens 113b, the convex lens 113c, and the convex lens 114a are provided for each of the imaging elements 111a and 111b. After light enters the imaging unit 110 through the concave lens 112a and the convex lens 112b included in the objective optical system 112, the light passes through the convex lens 113a, the concave lens 113b, and the convex lens 113c included in the variable-power optical system 113 and the convex lens 114a included in the focusing optical system, provided for each of the imaging elements 111a and 111b, in this order so as to be focused on the imaging element 111a or 111b. Although not illustrated in FIG. 2 to prevent the complexity of the drawing, each component provided in the casing 115 of the imaging unit 110 is supported by the casing 115 with various support members as appropriate.

One of the concave lens 112a and the convex lens 112b included in the objective optical system 112, e.g., the concave lens 112a located on the outer side with respect to the casing 115 is fixed to the casing 115. Conversely, for example, the convex lens 112b located on the inner side with respect to the casing 115 is configured to move in the z-axis direction (the optical-axis direction).

As illustrated in FIG. 2, for a support member 116 that supports the convex lens 112b with respect to the casing 115, a lead screw 117 that moves the support member 116 and the convex lens 112b in the z-axis direction and a motor 118 that rotates the lead screw 117 in the z-axis direction as a rotation-axis direction are provided. As the motor 118 is driven in accordance with an operation input to the above-described focus SW 152, the position of the convex lens 112b in the optical axis is moved so that the focal length of the imaging unit 110 is adjusted.

The motor 118 is provided with an encoder 119 that detects the rotating speed of the motor 118. A detection value of the encoder 119 is provided to the controller 140 as appropriate. As a detection value of the encoder 119 is the value indicating the position of the convex lens 112b in the optical axis, the controller 140 may calculate the focal length and/or the working distance (WD) of the imaging unit 110 based on a detection value of the encoder 119.

In the description according to the above-described example, the convex lens 112b is configured to move while the concave lens 112a is fixed so that the focal length of the imaging unit 110 is adjusted; however, the example is not a limitation. To adjust the focal length of the imaging unit 110, the relative distance between the concave lens 112a and the convex lens 112b in the optical axis may be adjusted; therefore, one or both of the concave lens 112a and the convex lens 112b may be configured to be movable, and there is no limitation on the specific configuration. The moving system that moves one or both of the concave lens 112a and the convex lens 112b is not limited to the above-described example, and any known system may be used.

Some or all of the convex lens 113a, the concave lens 113b, and the convex lens 113c included in the variable-power optical system 113 are configured to move in the z-axis direction. The convex lens 113a, the concave lens 113b, and/or the convex lens 113c is moved in the optical axis so that the magnification of the image captured by the imaging unit 110 may be adjusted. Although not illustrated in FIG. 2 for simplification, the convex lens 113a, the concave lens 113b, and/or the convex lens 113c is provided with a moving system that moves the corresponding lens in the z-axis direction in the same manner as the convex lens 112b. The moving system is driven under the control of the controller 140 in accordance with an operation input to the above-described zoom SW 151 or the set value of the zoom magnification so that the position of the convex lens 113a, the concave lens 113b, and/or the convex lens 113c in the optical axis is moved, whereby the zoom magnification of the imaging unit 110 may be adjusted.

With reference back to FIG. 1, the supporting unit 120 supports the imaging unit 110, moves the imaging unit 110 in three dimensions, and fixes the position and the posture of the imaging unit 110 after movement. In the illustrated example, the supporting unit 120 is configured as a balance arm having six degrees of freedom. The first embodiment is not limited to this example. It is appropriate as long as the supporting unit 120 is configured to have at least six degrees of freedom, and it may be configured to have equal to or more than seven degrees of freedom, what is called a redundant degree of freedom. The supporting unit 120 does not always need to be formed as a balance arm. However, when the supporting unit 120 is formed as a balance arm and the imaging unit 110 and the supporting unit 120 are configured to have a balanced moment in whole, the imaging unit 110 may be moved with less external force and the operability for the operator may be improved.

The supporting unit 120 is provided with six rotation axes to enable six degrees of freedom. Hereinafter, for the convenience of explanation, the members forming each rotation axis are collectively referred to as a rotation axis unit. For example, the rotation axis unit includes a bearing, a shaft rotatably inserted into the bearing, a sensor unit that detects the state (e.g., the rotation angle) of the rotation axis, and a brake that restricts the rotation around the rotation axis. The configuration of the rotation axis unit may be different depending on whether the rotation axis is the active axis described later or a passive axis. As a parallelogram link system 240 described later may be configured as a rotation axis, the parallelogram link system 240 may be regarded as the rotation axis unit.

The supporting unit 120 includes rotation axis units 210, 220, 230, 250, and 260 (hereinafter abbreviated as the rotation axis units 210 to 260) corresponding to the respective rotation axes, the parallelogram link system 240, arms 271 to 274 connecting the rotation axis units 210 to 260 and the parallelogram link system 240, and a counter weight 280 that enables a balanced moment of the imaging unit 110 and the supporting unit 120 as a whole. In the following description, the respective rotation axes are denoted by a first axis O1 to a sixth axis O6. The rotation axis located closest to the imaging unit 110 is the first axis O1, and the rotation axis located closest to the base 130 is the sixth axis O6.

The rotation axis unit 210 is provided so as to rotate the imaging unit 110 around the rotation axis (the first axis O1), which substantially matches the optical axis of the imaging unit 110, as its rotation axis direction. The rotation axis unit 210 causes the imaging unit 110 to rotate around the first axis O1 so that the direction of the image captured by the imaging unit 110 is adjusted.

The rotation axis unit 210 includes a brake 211, the encoder 212, and an actuator 213. The encoder 212 detects the rotation angle around the first axis O1. The brake 211 is driven due to an operation on the above-described all-free SW 153 to restrict the rotation around the first axis O1 as appropriate. The actuator 213 includes an electric motor, such as a servomotor, and is driven under the control of the controller 140 to cause the rotation in the rotation axis unit 210 at a predetermined angle. The rotation angle in the rotation axis unit 210 is set by the controller 140 based on the rotation angle at each of the rotation axes O1 to O6 as a value for moving the imaging unit 110 such that, for example, the observation point 730 is not changed before and after the imaging unit 110 is moved. A rotation axis unit like the rotation axis unit 210, which is provided with an active driving system such as an actuator, may be configured as a rotation axis that allows the active rotation due to the control on the driving of the actuator. In this description, a rotation axis at which the rotary driving is actively controlled by a driving system is also referred to as an active axis.

While the brake 211 is operating, the rotation of the imaging unit 110 around the first axis O1 may be prevented even when for example an external force is manually applied by an operator. The rotation axis unit 210 may be configured as a rotation axis that allows the rotation in accordance with for example the direct manual operation of the operator when the supply of energy to an active driving system such as the actuator 213 is stopped so that the brake is not operating (e.g., the above-described all-free mode). In this description, the rotation axis that allows the rotation in accordance with the direct operation is also referred to as a passive axis.

The rotation axis unit 210 is coupled to one end of the arm 271 extending in a direction substantially perpendicular to the first axis O1. At the other end of the arm 271, the rotation axis unit 220 is provided, which is configured to rotate the arm 271 in the rotation axis direction (the direction of the second axis O2) that is the extending direction of the arm 271. The second axis O2 is arranged substantially perpendicular to the first axis O1 and, in the example illustrated in FIG. 1, is provided as a rotation axis substantially parallel to the y-axis. The rotation axis unit 220 causes the imaging unit 110 and the arm 271 to rotate around the second axis O2 as a rotation axis so as to adjust the position of the imaging unit 110 in the x-axis direction.

The rotation axis unit 220 includes a brake 221, the encoder 222, and an actuator 223. As the functions of the brake 221, the encoder 222, and the actuator 223 are the same as the functions of the brake 211, the encoder 212, and the actuator 213 included in the rotation axis unit 210, detailed descriptions are omitted.

The rotation axis unit 220 is coupled to one end of an arm 272 extending in a direction substantially perpendicular to each of the first axis O1 and the second axis O2. At the other end of the arm 272, the rotation axis unit 230 is provided, which is configured to rotate the arm 272 in the rotation axis direction (the direction of the third axis O3) that is the extending direction of the arm 272. The third axis O3 is arranged substantially perpendicular to the first axis O1 and the second axis O2 and, in the example illustrated in FIG. 1, is provided as a rotation axis substantially parallel to the x-axis. The rotation axis unit 230 rotates the imaging unit 110, the arm 271, and the arm 272 around the third axis O3 as a rotation axis to adjust the position of the imaging unit 110 in the y-axis direction. As is the case with the rotation axis unit 220, the rotation axis unit 230 includes a brake 231, the encoder 232, and an actuator 233. Thus, the third axis O3, which is the rotation axis corresponding to the rotation axis unit 230, operates as an active axis.

According to the first embodiment, the supporting unit 120 is configured such that all of the rotation axes (the first axis O1 to the sixth axis O6) may function as an active axis and at least one of the axes may function as a passive axis. In the example illustrated in FIG. 1, for example, when a control is performed with a passive axis, at least one of the first axis O1 to the sixth axis O6 is controlled to be a passive axis.

Figure 3:
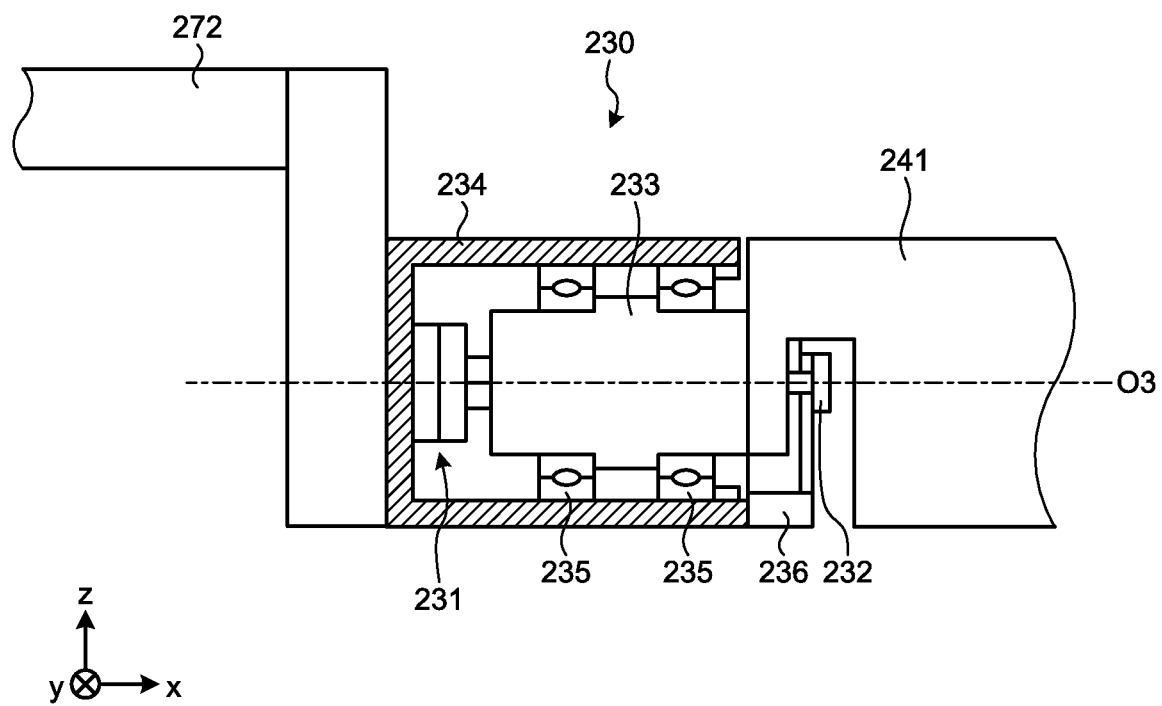
FIG. 3 is a diagram that illustrates an example of the configuration of a rotation axis unit corresponding to an active axis among rotation axis units illustrated in FIG. 1.

With reference to FIG. 3, the configurations of the rotation axis units 210 to 260 are described by using the rotation axis unit 230 as an example. By using the rotation axis unit 230 as an example, FIG. 3 is a cross-sectional view on the plane that passes through the rotation axis (the third axis O3) of the rotation axis unit 230 and is parallel to the rotation axis.

With reference to FIG. 3, inside a casing 234 of the rotation axis unit 230, the actuator 233 is provided such that the rotation axis (output shaft) is parallel to the third axis O3. Bearings 235 are provided between the side surface of the actuator 233 and the inner wall of the casing 234 so that, when the brake 231 described later is canceled, the actuator 233 is configured to rotate with respect to the casing 234.

The output shaft of the actuator 233 is coupled to the inner wall of the casing 234 in the direction of the third axis O3 through the brake 231. Thus, the casing 234 functions as a rotator that rotates in accordance with the driving of the actuator 233. The arm 272 is coupled to the outer wall surface of the casing 234 in the direction of the third axis O3 so that the arm 272 is rotated together with the casing 234 in accordance with the driving of the actuator 233. The brake 231 includes, for example, a mechanical clutch system. When the brake 231 is operating, the clutch system cancels the mechanical connection between the output shaft of the actuator 233 and the inner wall of the casing 234 so as not to transmit the driving of the actuator 233 to the casing 234, which is a rotator. Conversely, when the brake 231 is canceled, the clutch system mechanically connects the output shaft of the actuator 233 and the inner wall of the casing 234 so that the casing 234 is not rotated due to an external force and the casing 234 is rotated due to the driving of the actuator 233. The configuration of the brake 231 is not limited to this example, and other brake systems, such as an electromagnetic brake that electrically restricts the rotation of the casing 234, may be used as the brake 231.

An arm 241 forming the parallelogram link system 240 described later is coupled to the end of the actuator 233 at the opposite side of the output shaft via for example an undepicted bearing. That is, the actuator 233 is rotatably coupled to the arm 241. This allows the arm 272 to be rotatably coupled to the arm 241 via the rotation axis unit 230.

The encoder 232 is coupled, via a support member 236, to the rotation axis of the actuator 233 at the side where the arm 241 is connected. The encoder 232 detects the revolving speed and/or the rotation angle of the actuator 233. A detection value of the encoder 232 is provided to the controller 140. Based on a detection value of the encoder 232, the controller 140 may calculate the rotation angle around the third axis O3 with respect to the reference position, e.g., the arm 241.

Although the configuration of the rotation axis unit 230 is described above as an example of the rotation axis units 210 to 260, for example, the rotation axis unit 220 corresponding to an active axis as is the case with the rotation axis unit 230 may have the same configuration as that illustrated in FIG. 3. The rotation axis units 210, 250, and 260 corresponding to passive axes may have the same configuration as that illustrated in FIG. 3 from which the actuator 233 is omitted. As the actuator 233 is not provided in the rotation axis units 210, 250, and 260, it is difficult to use the brake 231 including the above-described mechanical clutch system; therefore, as the brake system, various systems capable of properly stopping the rotary movement of the rotation axis units 210, 250, and 260 may be used as appropriate. For example, electromagnetic brakes may be used as brake systems for the rotation axis units 210, 250, and 260.

With reference back to FIG. 1, the configuration of the supporting unit 120 is continuously described. The end of the rotation axis unit 230 on the side where the arm 272 is not connected is coupled to the parallelogram link system 240. The parallelogram link system 240 is formed of the four arms 241, 242, 243, and 244 arranged in the shape of a parallelogram and bearing parts 245, 246, 247, and 248 provided at the positions corresponding to substantially the vertices of the parallelogram.

Specifically, the rotation axis unit 230 is coupled to one end of the arm 241 extending in a direction substantially parallel to the third axis O3. That is, the arm 272 and the arm 241 are provided as arms extending in substantially the same direction. The bearing part 245 is provided at one end of the arm 241, and the bearing part 246 is provided at the other end thereof. The respective ends of the arms 242 and 243 are coupled to the bearing parts 245 and 246 so as to rotate around rotation axes (a fourth axis O4) that are substantially parallel to each other and inserted into the bearing parts 245 and 246.

The bearing parts 247 and 248 are provided at the respective other ends of the arms 242 and 243. The arm 244 is connected to the bearing parts 247 and 248 such that it is substantially parallel to the arm 241 and rotatable around the rotation axes (the fourth axis O4) inserted into the bearing parts 247 and 248. Thus, the four arms 241 to 244 and the four bearing parts 245 to 248 form the parallelogram link system 240.

Here, the arm 244 is formed to be longer than the arm 241, and one end thereof extends outward of the parallelogram link system 240. It is preferable that each of the arms 242 and 243 is formed to be longer than the interval between the bearing parts 247 and 248 of the arm 244. That is, it is preferable that the arms 242 and 243 are formed to be longer than the arm 241.

In the same manner as the rotation axis unit 210, the parallelogram link system 240 is provided with a brake 291, the encoder 292, and an actuator 293. In the example illustrated in FIG. 2, at the bearing part 247, the brake 291 is provided to restrict the rotation of the parallelogram link system 240 around the fourth axis O4. At the bearing part 245 of the parallelogram link system 240, the encoder 292 is provided to detect the rotation angle of the parallelogram link system 240 around the fourth axis O4. The output shaft of the actuator 293 is coupled to the inner wall of the casing via the brake 291 in the direction of the fourth axis O4. The location positions of the brake 291, the encoder 292, and the actuator 293 are not limited to this example, and they may be provided at any of the four bearing parts 245 to 248 of the parallelogram link system 240.

At a part apart from the end of the arm 242, in which the bearing part 247 is provided, by a predetermined distance, the rotation axis unit 250 is provided to rotatably support the parallelogram link system 240 in the rotation axis direction (the direction of a fifth axis O5) that is a direction perpendicular to the extending direction of the arm 242. The fifth axis O5 is a rotation axis substantially parallel to the fourth axis O4 and, in the example illustrated in FIG. 1, it is provided as a rotation axis substantially parallel to the y-axis. The rotation axis unit 250 is provided with a brake 251 that restricts the rotation around the fifth axis O5, the encoder 252 that detects the rotation angle around the fifth axis O5, and an actuator 253. The rotation axis unit 250 is coupled to one end of an arm 273 extending in the z-axis direction so that the parallelogram link system 240 is configured to rotate with respect to the arm 273 via the rotation axis unit 250.

The arm 273 has substantially an L shape, and the side thereof opposite to the side where the rotation axis unit 250 is provided is bent so as to be substantially parallel to the floor surface. The surface of the arm 273, which is substantially parallel to the floor surface, is provided with the rotation axis unit 260 that may rotate the arm 273 around the rotation axis (the sixth axis O6) perpendicular to the fifth axis O5. In the example illustrated in FIG. 1, the sixth axis O6 is provided as a rotation axis substantially parallel to the z-axis. The rotation axis unit 260 is provided with a brake 261 that restricts the rotation around the sixth axis O6, the encoder 262 that detects the rotation angle around the sixth axis O6, and an actuator 263. One end of an arm 274 extending in a vertical direction is inserted into the rotation axis unit 260, and the other end of the arm 274 is coupled to the base 130.

The counter weight 280 (counter balance 280) is integrally attached to the end of the arm 244 extending outward of the bearing part 248 placed diagonally to the bearing part 245 provided at the side of the parallelogram link system 240 where the rotation axis unit 230 is coupled. The mass and the location position of the counter weight 280 are adjusted so as to cancel the rotational moment generated around the fourth axis O4 and the rotational moment generated around the fifth axis O5 due to the mass of each component (i.e., the imaging unit 110, the rotation axis units 210, 220, and 230, and the arms 271 and 272) provided at the distal end side of the parallelogram link system 240. The counter weight 280 is removable. For example, in a case where some types of the counter weights 280 having different masses from each other are prepared and the component provided at the distal end side of the parallelogram link system 240 is changed, the counter weight 280 may be selected as appropriate so as to cancel the rotational moment in accordance with the change.

The location position of the rotation axis unit 250 corresponding to the fifth axis O5 is adjusted such that the center of gravity of each component (i.e., the imaging unit 110, the rotation axis units 210, 220, and 230, the arms 271 and 272, and the parallelogram link system 240) provided at the distal end side of the rotation axis unit 250 is located on the fifth axis O5. The location position of the rotation axis unit 260 corresponding to the sixth axis O6 is adjusted such that the center of gravity of each component (i.e., the imaging unit 110, the rotation axis units 210, 220, 230, and 250, the arms 271, 272, and 273, and the parallelogram link system 240) provided at the distal end side of the rotation axis unit 260 is located on the sixth axis O6. With the above-described configurations of the counter weight 280 and the rotation axis units 250 and 260, when the imaging unit 110 is directly moved with the operator's hand, the imaging unit 110 may be moved with a little force as if in zero gravity. Therefore, the user's operability may be improved.

The configuration of the supporting unit 120 is described above. As described above, at the respective rotation axes of the supporting unit 120, the brakes 211, 221, 231, 291, 251, and 261 (hereinafter sometimes abbreviated as the brakes 211 to 261) are provided to restrict the rotation at the rotation axes. As the brakes 211 to 261 are controlled under the control of the controller 140, the operation mode of the supporting unit 120 is switched. A brake does not always need to be provided in an active axis. In a case where no brake is provided, the driving of the actuator is controlled to generate the torque so as to maintain the position (the rotation angle) of the rotation axis unit, whereby the rotation at the rotation axis unit may be stopped. Thus, according to the first embodiment, an active axis may be provided with no mechanical brake system, and a braking function may be provided by driving an actuator.

At the respective rotation axes of the supporting unit 120, the encoders 212, 222, 232, 292, 252, and 262 (hereinafter sometimes abbreviated as the encoders 212 to 262) are provided to detect the rotation angles at the rotation axes. Furthermore, at the respective rotation axes of the supporting unit 120, the actuators 213, 223, 233, 293, 253, and 263 (hereinafter sometimes abbreviated as the actuators 213 to 263) are provided. Detection values of the encoders 212 to 262 are provided to the controller 140 at a predetermined interval on an as-needed basis so that the controller 140 monitors the rotation angle at each rotation axis. The controller 140 may calculate the current states of the imaging unit 110 and the supporting unit 120, i.e., the positions and the postures of the imaging unit 110 and the supporting unit 120 based on the rotation angle at each rotation axis. When the observation mode is switched, the controller 140 controls the driving of the actuator in the rotation axis unit such that the working distance between the imaging unit 110 and the observation point 730 becomes the set working distance based on the calculated positions and postures of the imaging unit 110 and the supporting unit 120.

The supporting unit 120 according to the first embodiment may be configured as a balance arm. Therefore, when the imaging unit 110 is moved by the operator in the all-free mode, it may be easily moved with a little force. Thus, according to the first embodiment, higher operability may be ensured with a smaller and simpler configuration.

Although not illustrated or described in the above description, the medical observation apparatus 10 may further include the other configuration that may be provided in typical existing medical observation apparatuses. For example, the medical observation apparatus 10 may include: an input unit that may input, to the medical observation apparatus 10, various types of information, such as the information used for surgery or the information needed to control the driving of the medical observation apparatus 10; an output unit that presents various types of information described above to the operator in a visual or auditory manner; a communication unit that transmits and receives various types of information described above to and from an external unit; a storage unit that stores various types of information described above; and a record unit that writes various types of information described above in a removable recording medium or reads it from a removable recording medium.

Next, the operation of the medical observation apparatus 10 according to the first embodiment described above while in use is described. First, as preparation before usage (before surgery), the entire medical observation apparatus 10 is moved close to the surgery bed 710 by using the casters 131.

After the surgery starts, the operator first presses the all-free SW 153 while grasping the grip part of the imaging unit 110. For example, a configuration is such that the operation mode of the supporting unit 120 in the medical observation apparatus 10 is the fixed mode while the all-free SW 153 is not pressed and it is the all-free mode while the all-free SW 153 is pressed. When the all-free SW 153 is pressed, the brakes 211 to 261 in the rotation axis units 210 to 260 and the parallelogram link system 240 are canceled so that the imaging unit 110 may be moved in a flexible manner due to the direct manual operation of the operator. Thus, in the all-free mode, all the rotation axes operate as if they are passive axes.

The operator views for example the image captured by the imaging unit 110 and displayed on the display device and moves the imaging unit 110 while pressing the all-free SW 153 such that the surgery site is positioned in the field of view of the imaging unit 110. As described above, as the medical observation apparatus 10 is a balance arm, the imaging unit 110 may be easily moved by the operator with a little force. After the imaging unit 110 is moved to the appropriate position, for example, the position such that the surgery site (observation point) is in the center of the field of view, the operator releases the all-free SW 153. Thus, the brakes 211 to 261 in the rotation axis units 210 to 260 and the parallelogram link system 240 operate to shift the operation mode of the supporting unit 120 to the fixed mode.

In this state, the operator operates the zoom SW 151 and the focus SW 152 to adjust the magnification and the focal length of the imaging unit 110 as appropriate. The operator gives various types of treatments to the surgery site while viewing the captured image after adjustment.

As the operator moves the imaging unit 110 to adjust the field of view while pressing the all-free SW 153, it is preferable that the all-free SW 153 is provided at a position to be easily pressed while the grip part of the imaging unit 110 is gripped.

Figure 4:
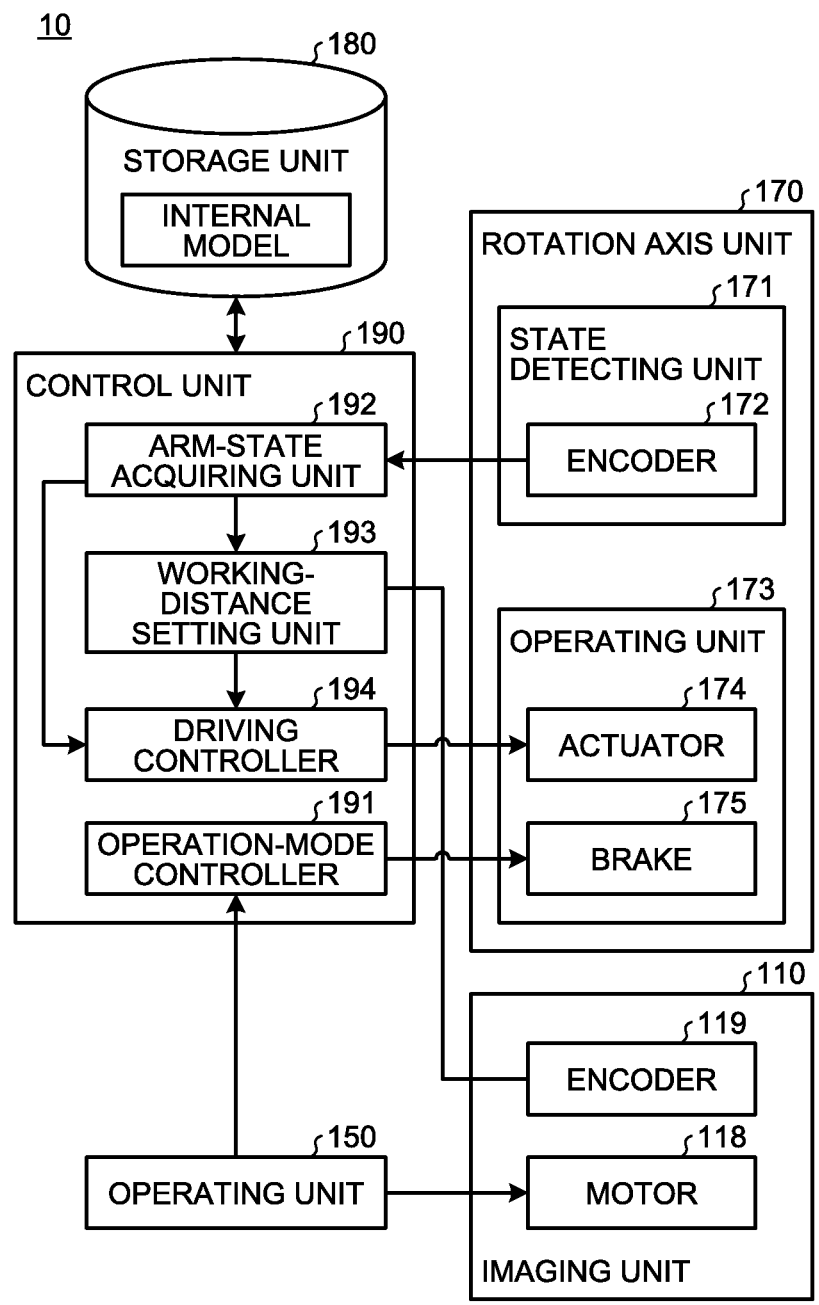
FIG. 4 is a block diagram that illustrates a configuration of the medical observation apparatus according to the first embodiment.

Next, with reference to FIG. 4, a functional configuration of the medical observation apparatus 10 according to the first embodiment described with reference to FIG. 1 is described. FIG. 4 is a functional block diagram that illustrates an example of the functional configuration of the medical observation apparatus 10 according to the first embodiment. The medical observation apparatus 10 includes the imaging unit 110, an operating unit 150, a rotation axis unit 170, a storage unit 180, and a control unit 190.

The imaging unit 110 is for example a microscope to capture the surgery site of a patient. The imaging unit 110 corresponds to the imaging unit 110 illustrated in FIG. 1 and FIG. 2. The imaging unit 110 includes: the motor 118 that moves the position of the convex lens 112b of the objective optical system in the optical axis; and the encoder 119 that detects the rotating speed of the motor 118 (see FIG. 2). The magnification and the focal length of the imaging unit 110 are adjusted in accordance with an operation input to the operating unit 150 (i.e., an operation to the zoom SW 151 and the focus SW 152). For example, the motor 118 is driven in accordance with the pressing of the zoom SW 151 so that the focal length of the imaging unit 110 is adjusted. The encoder 119 detects the rotating speed of the motor 118 and provides the detection value to a working-distance setting unit 193 described later in the control unit 190. According to the first embodiment, the imaging unit 110 may omit a microscope and may include other devices having an imaging function, such as a camera.

The operating unit 150 is an input interface that receives the operator's operation input to the medical observation apparatus 10. The operating unit 150 includes a device operated by the operator, such as a mouse, keyboard, touch panel, button, switch, or lever. The operator may input various types of information to the medical observation apparatus 10 or input various types of instructions via the operating unit 150. The operating unit 150 corresponds to the zoom SW 151, the focus SW 152, and the all-free SW 153 in the configuration illustrated in FIG. 1. For example, when the user presses the zoom SW 151 or the focus SW 152, the magnification or the focal length of the imaging unit 110 may be adjusted in response to the operation. When the user presses the all-free SW 153, the information indicating that the switch has been pressed is provided to an operation-mode controller 191 described later in the control unit 190 so that the operation mode of the supporting unit (arm unit) of the medical observation apparatus 10 is controlled.

The rotation axis unit 170 represents the function corresponding to the member that forms the rotation axis provided in the supporting unit of the medical observation apparatus 10. The rotation axis unit 170 represents the function of each rotation axis unit corresponding to an active axis.

The rotation axis unit 170 includes, as its functions, a state detecting unit 171 and an operating unit 173. The state detecting unit 171 detects the state of the rotation axis unit 170, i.e., the rotation angle of the rotation axis unit 170. The state detecting unit 171 includes an encoder 172 that may detect the rotation angle of the rotation axis unit 170. The state detecting unit 171 provides an arm-state acquiring unit 192 described later of the control unit 190 with the value of the rotation angle detected by the encoder 172.

The operating unit 173 has a function regarding the rotation operation of the rotation axis unit 170. The operating unit 173 includes: an actuator 174 that rotationally drives the rotation axis unit 170 around the rotation axis; and a brake 175 that restricts the rotation of the rotation axis unit 170. Thus, the operating unit 173 has the function to actively drive the rotation axis unit 170 like the actuator 174.

The operating unit 173 controls the operation of each unit in accordance with the operation mode selected responsive to a command from the operation-mode controller 191 described later in the control unit 190. For example, when the observation mode is switched from the normal observation mode to the special-light observation mode, the operating unit 173 drives the imaging unit 110 and the supporting unit 120 so as to move them to a position such that the working distance of the imaging unit 110 becomes the set working distance.

For example, the operating unit 173 causes the brake 175 to operate or be canceled in accordance with the operation mode. Specifically, when the operation mode is the fixed mode, the operating unit 173 causes the brake 175 to operate so as to prevent the free rotation of the rotation axis unit 170 due to an external force. Conversely, when the operation mode is the all-free mode, the operating unit 173 causes the brake 175 to be canceled so as to enable the free rotation of the rotation axis unit 170 in accordance with the operator's direct operation.

The storage unit 180 includes, for example, a magnetic storage device, such as an HDD (hard disk drive), a semiconductor storage device, an optical storage device, or a magnetooptical storage device, and stores various types of information processed by the medical observation apparatus 10. For example, the storage unit 180 may store various types of information regarding the driving control of the supporting unit 120 in the medical observation apparatus 10. The various types of information regarding the driving control include, for example, various types of information such as the internal model corresponding to the supporting unit 120, a value detected by the encoder 119 of the imaging unit 110, a value detected by the encoder 172 of the state detecting unit 171, the information about the arm state described later, the positional information on an observation point, the working distance for each observation mode, or the information regarding the control value of the actuator 174 in the operating unit 173. The control unit 190 is configured to access the storage unit 180 so that the control unit 190 may perform various calculations by using various types of information stored in the storage unit 180.

The control unit 190 includes a processor such as a CPU or a DSP, and performs an operation in accordance with a predetermined program to control the operation of the medical observation apparatus 10. The control unit 190 and the storage unit 180 may be implemented by using the controller 140 illustrated in FIG. 1. For example, the function of the storage unit 180 may be performed by a storage device, such as a memory, provided in the controller 140, or the function of the control unit 190 may be performed by a processor provided in the controller 140.

The control unit 190 includes, as its functions, the operation-mode controller 191, the arm-state acquiring unit 192, the working-distance setting unit 193, and a driving controller 194.

The operation-mode controller 191 controls the observation mode of the medical observation apparatus 10 and the operation mode of the supporting unit 120. The operation-mode controller 191 determines any of the observation modes for the normal observation and the special light observation in accordance with an operation input from the operator via the operating unit 150 and changes various processing settings, e.g., a capturing condition or an image processing parameter, so as to enable the determined observation mode.

The operation-mode controller 191 determines the operation mode of the supporting unit 120 in accordance with an operation input from the operator via the operating unit 150 and gives an instruction to the operating unit 173 in the rotation axis unit 170 so as to enable the determined operation mode. For example, when the all-free SW 153 is not pressed, the operation-mode controller 191 determines that the operation mode of the supporting unit 120 is set to the fixed mode and gives an instruction to the operating unit 173 so as to operate the brake 175. For example, when the all-free SW 153 is pressed, the operation-mode controller 191 determines that the operation mode of the supporting unit 120 is set to the all-free mode and gives an instruction to the operating unit 173 so as to cancel the brake 175.

The arm-state acquiring unit 192 acquires the state (arm state) of the supporting unit 120 based on the state of the rotation axis unit 170. The arm state may represent the position and the posture of the supporting unit 120. The arm-state acquiring unit 192 acquires the arm state based on the detection value (i.e., the rotation angle of the rotation axis unit 170) of the encoder 172 provided by the state detecting unit 171 and the internal model stored in the storage unit 180. As the internal model includes geometric parameters of the supporting unit 120, i.e., the information on the location position of the rotation axis in the supporting unit 120, and the length, the shape, or the like, of the arms 271 to 274, the arm-state acquiring unit 192 may acquire the arm state based on the detection value of the encoder 172 and the internal model.

The working-distance setting unit 193 extracts the working distance of the observation mode to be set from the working distance stored in the storage unit 180 or the working distance input and set via the operating unit 150. The working-distance setting unit 193 may set the working distance input after the operator's observation-mode switching operation, or the like, as the working distance of the observation mode to be switched. The working-distance setting unit 193 provides the information on the set working distance to the driving controller 194.

The driving controller 194 moves the imaging unit 110 and the supporting unit 120 such that the distance between the imaging unit 110 and the observation target (the observation point 730) after the switching of the observation mode becomes the working distance corresponding to the observation mode. When an instruction to switch the observation mode is input, for example, the driving controller 194 refers to the storage unit 180 to extract the working distance corresponding to the set observation mode and then controls the driving of the imaging unit 110 and the supporting unit 120 such that the distance between the imaging unit 110 and the observation target becomes the extracted working distance. The driving controller 194 controls the light source device 200 so as to output the light having the wavelength band corresponding to the observation mode.

Figure 5:
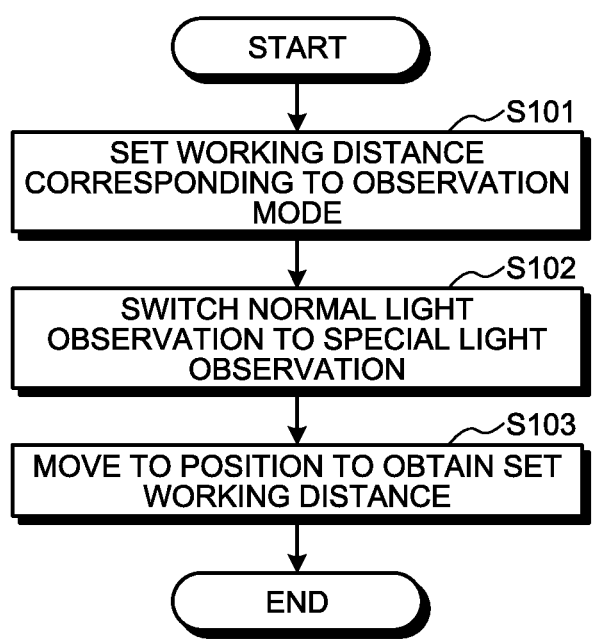
FIG. 5 is a flowchart that illustrates an observation-mode switching process performed by the medical observation apparatus according to the first embodiment.

Then, with reference to FIG. 5, the observation-mode switching process performed by the medical observation apparatus is described. FIG. 5 is a flowchart that illustrates the observation-mode switching process performed by the medical observation apparatus according to the first embodiment. The flowchart illustrated in FIG. 5 illustrates the flow of the process after an instruction is input to switch the observation mode from the normal observation mode to the special-light observation mode (e.g., any of NBI, IRI, AFI, and PDD described above).

First, the working-distance setting unit 193 sets the working distance of the observation mode to be switched (Step S101). The working-distance setting unit 193 refers to the storage unit 180 and sets the working distance of the observation mode. When the working distance of the observation mode, which is the target to be set, has not been set, the control unit 190 notifies the operator that the working distance has not been set.

Then, the operation-mode controller 191 switches the normal-light observation mode to the special-light observation mode (Step S102). Specifically, the operation-mode controller 191 sets the capturing condition (e.g., the exposure time period, the frame rate, or the gain) corresponding to the special-light observation mode, the wavelength band of the illumination light output from the light source device 200, or the image processing condition. At this point, the operation-mode controller 191 acquires the working distance corresponding to the set observation mode.

After the operation-mode controller 191 has completely set each condition of the observation mode, the driving controller 194 moves the position of the imaging unit 110 such that the distance between the imaging unit 110 and the observation target becomes the acquired working distance (Step S103). At this point, under the control of the control unit 190, the supporting unit 120 is driven together with the imaging unit 110 based on the posture of the supporting unit 120 acquired by the arm-state acquiring unit 192.

Figure 6:
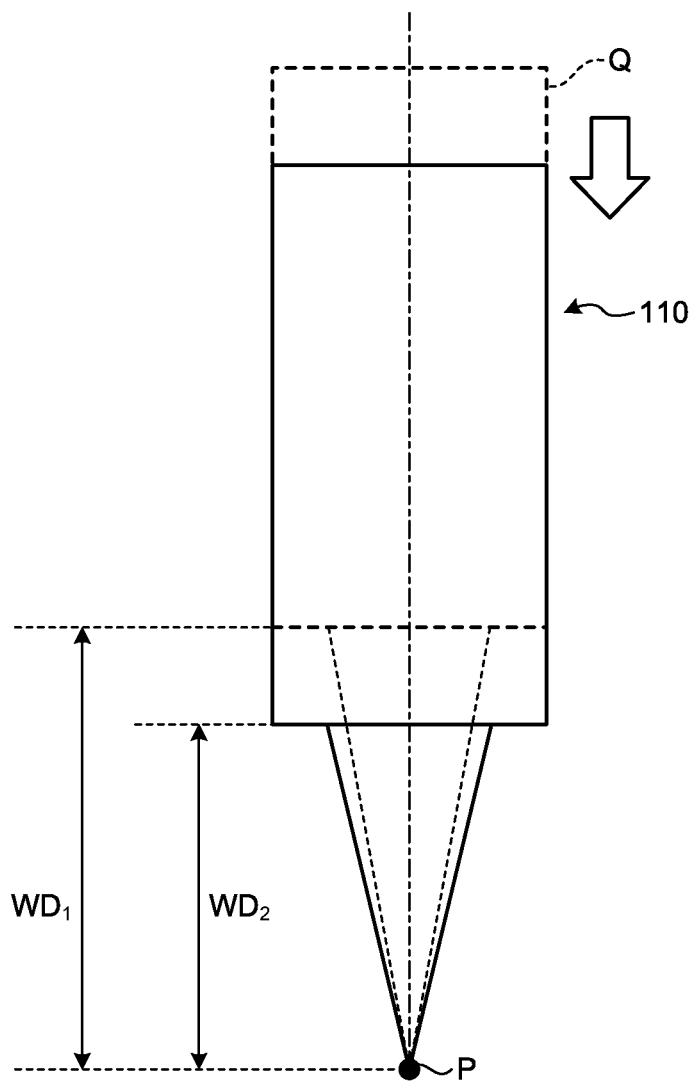
FIG. 6 is a diagram that illustrates a process to change a working distance during the observation mode switching performed by the medical observation apparatus according to the first embodiment.

FIG. 6 is a diagram that illustrates a process to change the working distance during the observation mode switching performed by the medical observation apparatus according to the first embodiment. In FIG. 6, the solid line indicates the location of the imaging unit 110 during the special-light observation mode, and a dashed line Q indicates the position of the imaging unit 110 during the normal observation mode.

Generally, in the special light observation, the amount of light detectable by a microscope unit is small as compared to that in the normal observation. As described above, for example, the amount of illumination light is small in the NBI, and the amount of fluorescence generated by an observed region is small with respect to excitation light in the AFI. Therefore, according to the first embodiment, the working distance in the special-light observation mode is shorter than the working distance in the normal observation mode so that the lighting intensity at the imaging surface is increased. Specifically, when the working distance in the normal observation mode is $WD_1$ and the working distance in the special-light observation mode is $WD_2$, $WD_1 > WD_2$. The working distance is the distance from the end of the imaging unit 110 at the side of the light-receiving surface for the observation light to an observation point P. For example, the minimum possible working distance of the imaging unit 110 is set as the working distance $WD_2$. The working distance $WD_2$ may be set for each of, for example, NBI, IRI, AFI, and PDD.

Then, the special light observation is performed with the special light output from the light source device 200.

According to the first embodiment described above, when the normal observation mode is switched to the special-light observation mode, the distance (working distance) between the imaging unit 110 and the observation point is controlled such that the working distance in the special-light observation mode is shorter than the working distance set in accordance with the observation mode, e.g., the working distance in the normal observation mode, so that the lighting intensity at the imaging surface during the special-light observation mode may be increased and a reduction in the image quality during the special light observation may be prevented. A high lighting intensity at the imaging surface allows a large signal value per hour as compared to that in the case of a long working distance, which may result in a shorter capturing time and a higher frame rate.

Modification of the First Embodiment

Figure 7:
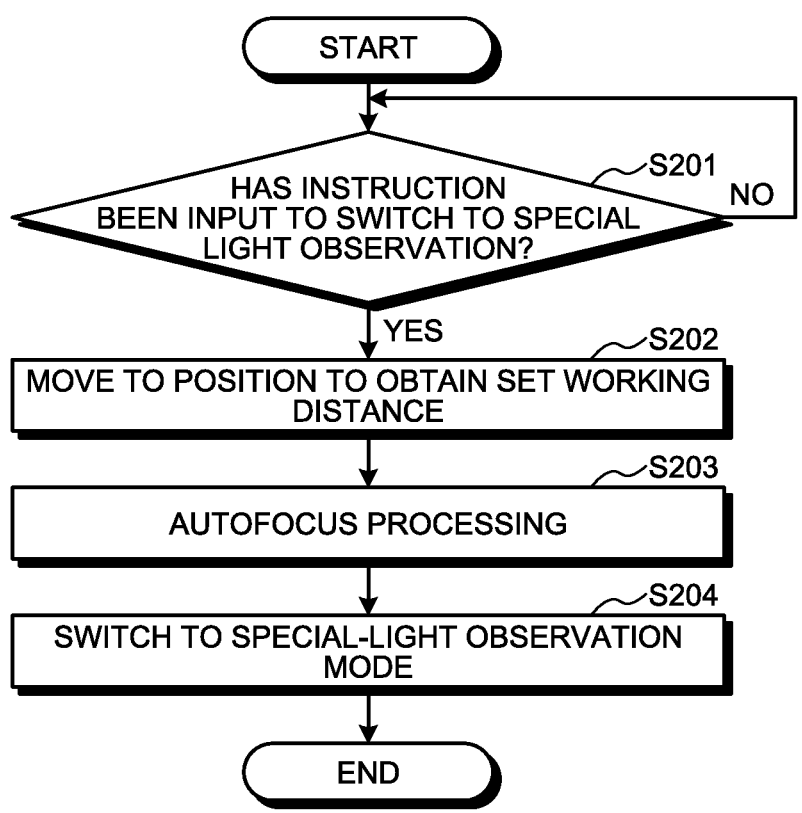
FIG. 7 is a flowchart that illustrates an observation-mode switching process performed by the medical observation apparatus according to a modification of the first embodiment.

Then, a modification of the above-described first embodiment is described. FIG. 7 is a flowchart that illustrates an observation-mode switching process performed by the medical observation apparatus according to a modification of the first embodiment. As the modification is the same as the above-described first embodiment in other than the observation-mode switching process performed by the medical observation apparatus, the descriptions of the configuration, and the like, are omitted.

The control unit 190 determines whether an instruction has been input to switch the observation mode from the normal observation mode to the special-light observation mode (e.g., any of NBI, IRI, AFI, and PDD described above) (Step S201). When no instruction has been input to switch to the special-light observation mode (Step S201: No), the control unit 190 repeatedly checks whether an instruction has been input to switch the observation mode. Conversely, when an instruction has been input to switch to the special-light observation mode (Step S201: Yes), the control unit 190 proceeds to Step S202.

At Step S202, the working-distance setting unit 193 sets, as the working distance, the working distance corresponding to the special-light observation mode to be switched, and the driving controller 194 moves the imaging unit 110 to the position so as to obtain the set working distance.

Then, the driving controller 194 performs the autofocus processing so that there is a focus on the observation point with the moved imaging unit 110 (Step S203). At this point, the autofocus processing is performed in the normal observation mode (white light).

Then, the operation-mode controller 191 switches the observation mode from the normal-light observation mode to the special-light observation mode (Step S204). Specifically, the operation-mode controller 191 sets the capturing condition (e.g., the exposure time period or the frame rate) corresponding to the special-light observation mode, the wavelength band of the illumination light output from the light source device 200, or the image processing condition.

According to the modification described above, to switch the normal observation mode to the special-light observation mode, after the imaging unit 110 is moved to obtain the working distance set corresponding to the special-light observation mode, autofocus processing is performed with white light so that focusing is conducted with white light before a transition is made to the special-light observation mode, whereby a higher lighting intensity may be obtained at the imaging surface during the special-light observation mode, a reduction in the image quality during the special light observation may be prevented, and the focus state may be ensured after a transition is made to the special-light observation mode.

Second Embodiment

Figure 8:
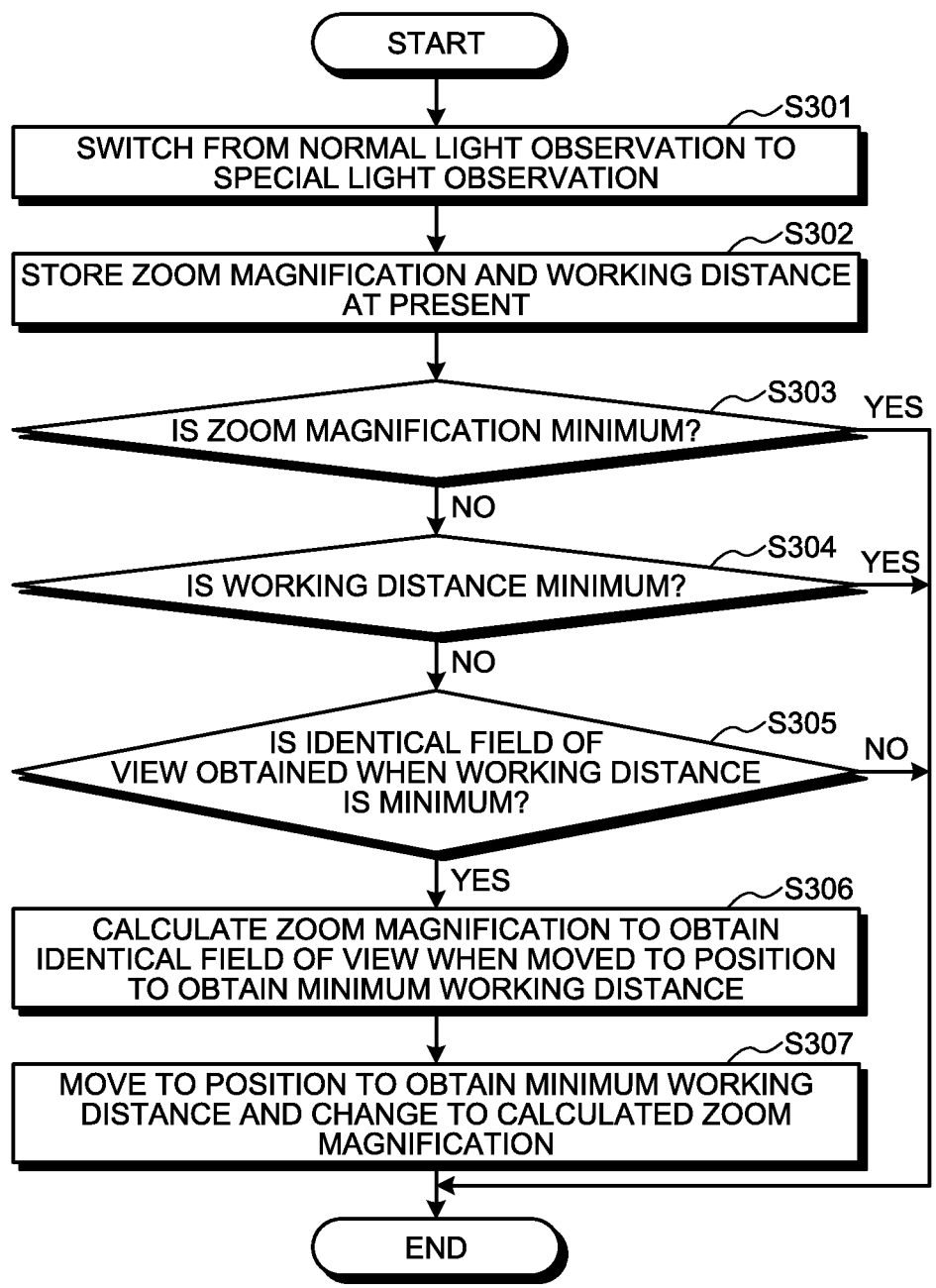
FIG. 8 is a flowchart that illustrates an observation-mode switching process performed by the medical observation apparatus according to a second embodiment.

Next, a second embodiment is described. FIG. 8 is a flowchart that illustrates an observation-mode switching process performed by the medical observation apparatus according to the second embodiment. As the second embodiment is the same as the above-described first embodiment in other than the observation-mode switching process performed by the medical observation apparatus, the descriptions of the configuration, and the like, are omitted. The flowchart illustrated in FIG. 8 illustrates the flow of the process after an instruction is input to switch the observation mode from the normal observation mode to the special-light observation mode (e.g., any of NBI, IRI, AFI, and PDD described above). According to the second embodiment, when a switchover is made to the special-light observation mode, the working distance is the minimum possible working distance of the imaging unit 110. It may be set to a working distance shorter than that in the normal observation mode instead of the minimum working distance.

The operation-mode controller 191 switches the observation mode from the normal-light observation mode to the special-light observation mode (Step S301). Specifically, the operation-mode controller 191 sets the capturing condition (e.g., the exposure time period or the frame rate) corresponding to the special-light observation mode, the wavelength band of the illumination light output from the light source device 200, or the image processing condition.

Then, the operation-mode controller 191 stores the zoom magnification and the working distance at present in the storage unit 180 (Step S302). At this point, the operation-mode controller 191 stores, in the storage unit 180, the zoom magnification and the working distance immediately before the normal observation mode is switched to the special-light observation mode.

At Step S303 subsequent to Step S302, the operation-mode controller 191 determines whether the zoom magnification stored at Step S302 is the minimum possible magnification of the imaging unit 110. When the zoom magnification is the minimum (Step S303: Yes), the operation-mode controller 191 terminates the observation-mode switching process without adjusting the working distance corresponding to the observation mode. Conversely, when the zoom magnification is not the minimum (Step S303: No), the operation-mode controller 191 proceeds to Step S304.

At Step S304, the operation-mode controller 191 determines whether the current working distance is the minimum possible working distance of the imaging unit 110. When the working distance is the minimum (Step S304: Yes), the operation-mode controller 191 terminates the observation-mode switching process without adjusting the working distance corresponding to the observation mode. Conversely, when the working distance is not the minimum (Step S304: No), the operation-mode controller 191 proceeds to Step S305.

At Step S305, the operation-mode controller 191 determines whether the field of view identical to the field of view in the normal observation mode is obtained even when the working distance is the minimum corresponding to the special-light observation mode. When it is determined that the field of view identical to the field of view in the normal observation mode is not obtained when the working distance is the minimum (Step S305: No), the operation-mode controller 191 terminates the observation-mode switching process without adjusting the working distance corresponding to the observation mode. Conversely, when it is determined that the field of view identical to the field of view in the normal observation mode is obtained when the working distance is the minimum (Step S305: Yes), the operation-mode controller 191 proceeds to Step S306.

Figure 9:
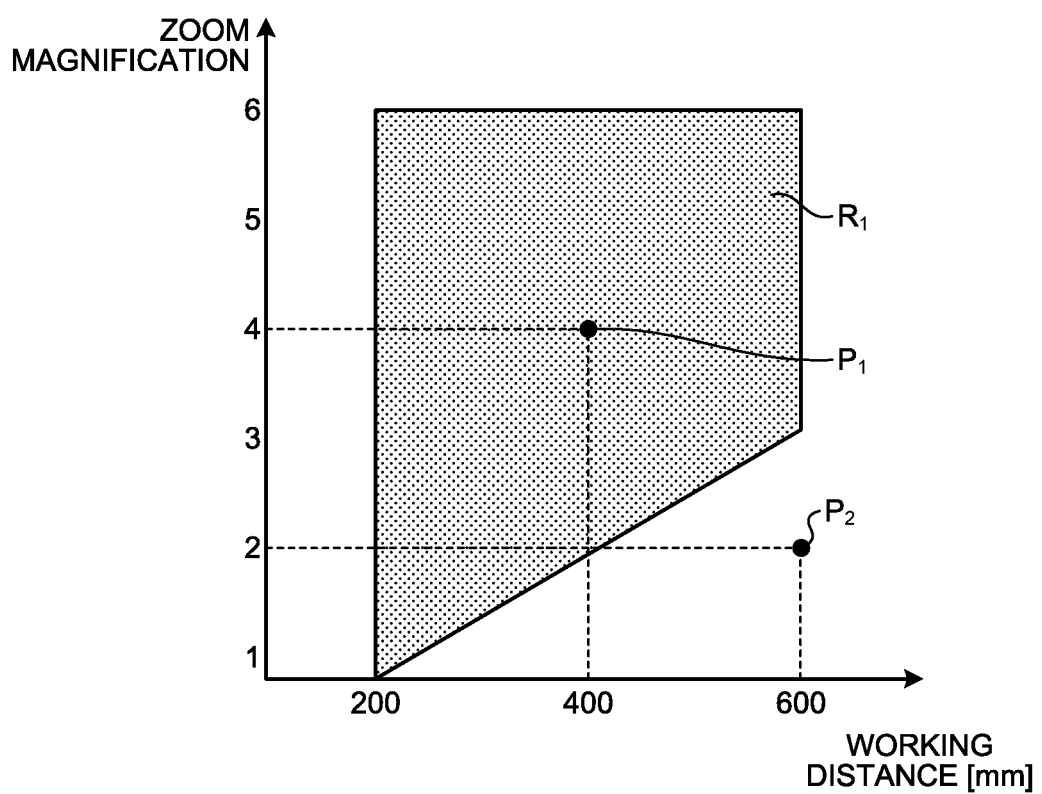
FIG. 9 is a diagram that illustrates a process to set a working distance and a zoom magnification during the observation mode switching performed by the medical observation apparatus according to the second embodiment.

Here, a process to determine the identical field of view at Step S305 is described with reference to FIG. 9. FIG. 9 is a diagram that illustrates a process to set the working distance and the zoom magnification during the observation mode switching performed by the medical observation apparatus according to the second embodiment. In the case assumed in FIG. 9, the working distance of the imaging unit 110 may be set to 200 mm to 600 mm and the zoom magnification may be set to one-fold to six-fold. An area $R_1$ illustrated in FIG. 9 is an area in which the identical field of view as that in the normal observation is obtained even when the working distance is the minimum. For example, a point $P_1$ corresponding to a working distance of 400 mm and a zoom magnification of four-fold is located within the area $R_1$, the operation-mode controller 191 determines that the field of view identical to the field of view in the normal observation mode is obtained even when the working distance is the minimum in accordance with the special-light observation mode. Conversely, as a point $P_2$ corresponding to a working distance of 600 mm and a zoom magnification of two-fold is located outside the area $R_1$, the operation-mode controller 191 determines that the field of view identical to the field of view in the normal observation mode is not obtained when the working distance is the minimum.

At Step S306, the operation-mode controller 191 calculates the zoom magnification to obtain the field of view identical to that in the normal observation when the working distance is the minimum in accordance with the special-light observation mode. The operation-mode controller 191 calculates the zoom magnification to obtain the identical field of view based on the set working distance and the angle of view at each zoom magnification at that time. As the working distance in the special light observation is shorter than that in the normal observation, the distance between the imaging unit 110 and the observation point is shorter, and in order to obtain the identical field of view, a small zoom magnification as compared with that in the normal observation is calculated.

At Step S307 subsequent to Step S306, the working-distance setting unit 193 sets, as a working distance, the working distance corresponding to the special-light observation mode to be switched, and the driving controller 194 moves the imaging unit 110 to a position to obtain the set working distance. The operation-mode controller 191 sets, as a zoom magnification, the zoom magnification calculated at Step S306, and the driving controller 194 controls the optical system of the imaging unit 110 so as to obtain the set zoom magnification.

According to the second embodiment described above, when the normal observation mode is switched to the special-light observation mode, the distance (working distance) between the imaging unit 110 and the observation point is controlled such that the working distance in the special-light observation mode is shorter than the working distance set in accordance with the observation mode, e.g., the working distance in the normal observation mode, so that the lighting intensity at the imaging surface during the special-light observation mode may be increased and a reduction in the image quality during the special light observation may be prevented.

Furthermore, according to the second embodiment, when the normal observation mode is switched to the special-light observation mode, the zoom magnification is adjusted so that a control is performed to obtain the field of view identical to that in the normal observation, whereby the special light observation may be conducted while the field of view in the normal observation is maintained.

Third Embodiment

Figure 10:
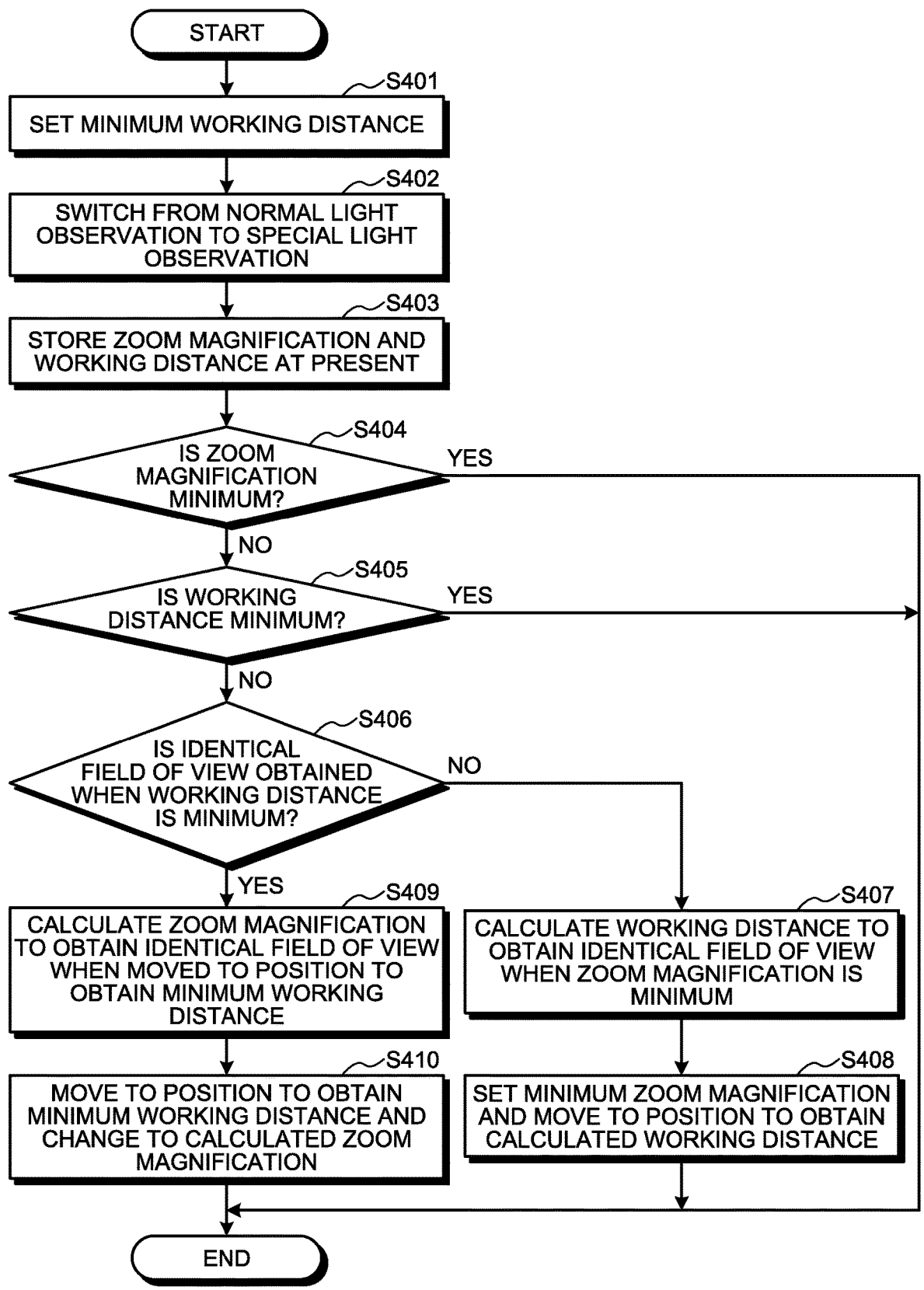
FIG. 10 is a flowchart that illustrates the observation-mode switching process performed by the medical observation apparatus according to a third embodiment.

Next, a third embodiment is described. FIG. 10 is a flowchart that illustrates the observation-mode switching process performed by the medical observation apparatus according to the third embodiment. As the third embodiment is the same as the above-described first embodiment in other than the observation-mode switching process performed by the medical observation apparatus, the descriptions of the configuration, and the like, are omitted. The flowchart illustrated in FIG. 10 illustrates the flow of the process after an instruction is input to switch the observation mode from the normal observation mode to the special-light observation mode (e.g., any of NBI, IRI, AFI, and PDD described above).

First, the working-distance setting unit 193 sets the working distance of the observation mode to be switched (Step S401). The working-distance setting unit 193 refers to the storage unit 180 in the same manner as at Step S101 to set the working distance of the observation mode.

The operation-mode controller 191 switches the observation mode from the normal-light observation mode to the special-light observation mode (Step S402). Specifically, the operation-mode controller 191 sets the capturing condition (e.g., the exposure time period or the frame rate) corresponding to the special-light observation mode, the wavelength band of the illumination light output from the light source device 200, or the image processing condition.

Then, the operation-mode controller 191 stores the zoom magnification and the working distance at present in the storage unit 180 (Step S403). At this point, the operation-mode controller 191 stores, in the storage unit 180, the zoom magnification and the working distance immediately before the normal observation mode is switched to the special-light observation mode.

At Step S404 subsequent to Step S403, the operation-mode controller 191 determines whether the zoom magnification stored at Step S403 is the minimum possible magnification of the imaging unit 110. When it is determined that the zoom magnification is the minimum (Step S404: Yes), the operation-mode controller 191 terminates the observation-mode switching process without adjusting the working distance corresponding to the observation mode. Conversely, when it is determined that the zoom magnification is not the minimum (Step S404: No), the operation-mode controller 191 proceeds to Step S405.

At Step S405, the operation-mode controller 191 determines whether the current working distance is the minimum possible working distance of the imaging unit 110. When it is determined that the working distance is the minimum (Step S405: Yes), the operation-mode controller 191 terminates the observation-mode switching process without adjusting the working distance corresponding to the observation mode. Conversely, when it is determined that the working distance is not the minimum (Step S405: No), the operation-mode controller 191 proceeds to Step S406.

At Step S406, the operation-mode controller 191 determines whether the field of view identical to the field of view in the normal observation mode is obtained even when the working distance is the minimum corresponding to the special-light observation mode. When it is determined that the field of view identical to the field of view in the normal observation mode is not obtained when the working distance is the minimum (Step S406: No), the operation-mode controller 191 proceeds to Step S407. Conversely, when it is determined that the field of view identical to the field of view in the normal observation mode is obtained when the working distance is the minimum (Step S406: Yes), the operation-mode controller 191 proceeds to Step S409.

At Step S407, the working-distance setting unit 193 calculates the working distance to obtain the field of view identical to the field of view in the normal observation when the zoom magnification is the minimum. At Step S408 subsequent to Step S407, the working-distance setting unit 193 sets, as a working distance, the working distance calculated at Step S407, and the driving controller 194 moves the imaging unit 110 to a position to obtain the set working distance. The operation-mode controller 191 sets, as a zoom magnification, the minimum zoom magnification, and the driving controller 194 controls the optical system of the imaging unit 110 to obtain the set zoom magnification.

At Step S409, in the same manner as at Step S306, the operation-mode controller 191 calculates the zoom magnification to obtain the field of view identical to that in the normal observation when the working distance is the minimum corresponding to the special-light observation mode.

At Step S410 subsequent to Step S409, the working-distance setting unit 193 sets, as a working distance, the working distance corresponding to the special-light observation mode to be switched, and the driving controller 194 moves the imaging unit 110 to a position to obtain the set working distance. The operation-mode controller 191 sets, as a zoom magnification, the zoom magnification calculated at Step S409, and the driving controller 194 controls the optical system of the imaging unit 110 to obtain the set zoom magnification.

According to the third embodiment described above, when the normal observation mode is switched to the special-light observation mode, the distance (working distance) between the imaging unit 110 and the observation point is controlled such that the working distance in the special-light observation mode is shorter than the working distance set in accordance with the observation mode, e.g., the working distance in the normal observation mode, so that the lighting intensity at the imaging surface during the special-light observation mode may be increased and a reduction in the image quality during the special light observation may be prevented.

Furthermore, according to the third embodiment, when the normal observation mode is switched to the special-light observation mode, the zoom magnification is adjusted so as to obtain the field of view identical to that in the normal observation, whereby the special light observation may be conducted while the field of view in the normal observation is maintained. Even in a case where it is difficult to obtain the field of view identical to the field of view during the normal observation by using the working distance set for the special-light observation mode and the zoom magnification, the working distance is set to obtain the identical field of view when the zoom magnification is the minimum, whereby the special light observation may be conducted while the field of view in the normal observation is maintained.

Although the embodiments for implementing the present disclosure are described above, the present disclosure is not limited to the above-described embodiments. For example, the supporting unit 120 may include at least one group of two arm units and a joint unit coupling the two arm units so as to rotate one of them relative to the other one.

In the case described according to the first embodiment to the third embodiment, the working distance is changed by using an instruction to switch the observation mode as a trigger; however, for example, the working distance may be changed in accordance with an operation performed by the operator. For example, the working distance to be set may be changed in a case where the operator observes an image and in a case where the operator actually gives treatment. For example, as for the set working distance, in order to ensure the image quality during observation, the working distance for observation is set to be shorter than the working distance for treatment. In this case, the controller 140 receives instruction information regarding the observation mode and the work details.

The imaging unit 110 may include one or three or more imaging elements. When the imaging unit 110 includes a single imaging element, a displayed image is a two-dimensional image.

In the case described according to the first embodiment, the controller 140 calculates the focal length and/or the working distance (WD) of the imaging unit 110 based on a detection value of the encoder 119; however, a configuration may be such that the distance is calculated by using an infrared laser, or the like.

The medical observation apparatus may be configured to hang down from the ceiling that is an installation area.

As described above, the present disclosure may include various embodiments, or the like, without departing from the technical idea described in the scope of claims.

As described above, the medical observation apparatus according to the present disclosure is advantageous in preventing a reduction in the image quality during special light observation.

According to the present disclosure, there is an advantageous effect of preventing a reduction in the image quality during special light observation.

Although the disclosure has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:
1. A medical observation apparatus comprising:
a camera configured to capture an observation object to output an imaging signal and including a zoom lens configured to change a zoom magnification;
a support configured to movably support the camera; and
controller circuitry configured to
control, when a normal observation mode with white light used to image the observation object is switched to a special-light observation mode with special light used to image the observation object, the support such that the camera is moved to a position so as to obtain a working distance between the camera and the observation object that is set for the special-light observation mode and that is shorter than a working distance between e camera and the observation object in the normal observation mode,
calculate a zoom magnification to obtain a field of view identical to a field of view in the normal observation mode with regard to a working distance between the camera and the observation object corresponding to the special-light observation mode; and move the camera to a position to obtain the working distance between the camera and the observation object corresponding to the special-light observation mode and change a magnification of the zoom lens to the calculated zoom magnification.

2. The medical observation apparatus according to claim 1, wherein when a field of view in the special-light observation mode obtained with the working distance between the camera and the observation object corresponding to the special-light observation mode and a minimum zoom magnification is not identical to a field of view in the normal observation mode, the controller circuitry is configured to:
calculate a working distance between the camera and the observation object to obtain a field of view identical to the field of view in the normal observation mode at the minimum zoom magnification, and
move the camera to a position to obtain the calculated working distance and change a magnification of the zoom lens to the minimum zoom magnification.

3. The medical observation apparatus according to claim 1, wherein the controller circuitry is configured to set a minimum possible working distance of the camera as a working distance between the camera and the observation object in the special-light observation mode.

4. The medical observation apparatus according to claim 1, wherein
the support includes rotation axes configured to allow operations with at least six degrees of freedom, and
each of the rotation axes of the support is an active axis that is controlled to be driven under control of the controller circuitry.

5. The medical observation apparatus according to claim 1, wherein an intensity of an imaging signal output in the normal observation mode is greater than an intensity of an imaging signal output in the special-light observation mode.

6. A medical apparatus for controlling a camera including a zoom lens and a support configured to movably support the camera, comprising:
controller circuitry configured to
receive an imaging signal of an observation object from the camera;
control, when a normal observation mode with white light used to image the observation object is switched to a special-light observation mode with special light used to image the observation object, the support such that the camera is moved to a position so as to obtain a working distance between the camera and the observation object that is set for the special-light observation mode and that is shorter than a working distance between the camera and the observation object in the normal observation mode,
calculate a zoom magnification to obtain a field of view identical to a field of view in the normal observation mode with regard to a working distance between the camera and the observation object corresponding to the special-light observation mode; and
move the camera to a position to obtain the working distance between the camera and the observation object corresponding to the special-light observation mode and change a magnification of the zoom lens to the calculated zoom magnification.

7. The medical apparatus according to claim 6, wherein when a field of view in the special-light observation mode obtained with the working distance between the camera and the observation object corresponding to the special-light observation mode and a minimum zoom magnification is not identical to a field of view in the normal observation mode, the controller circuitry is configured to:
calculate a working distance between the camera and the observation object to obtain a field of view identical to the field of view in the normal observation mode at the minimum zoom magnification, and
move the camera to a position to obtain the calculated working distance and change a magnification of the zoom lens to the mum zoom magnification.

8. The medical observation method according to claim 7, wherein when a field of view in the special-light observation mode obtained with the working distance between the camera and the observation object corresponding to the special-light observation mode and a minimum zoom magnification is not identical to a field of view in the normal observation mode, the processes further comprising:
calculating a working distance between the camera and the observation object to obtain a field of view identical to the field of view in the normal observation mode at the minimum zoom magnification, and
moving the camera to a position to obtain the calculated working distance and change a magnification of the zoom lens to the minimum zoom magnification.

9. A medical observation method implemented by a computer to perform processes for controlling a camera including a zoom lens and a support configured to movably support the camera, the processes comprising:
receiving an imaging signal of an observation object from the camera,
controlling, when a normal observation mode with white light used to image the observation object is switched to a special-light observation mode with special light used to image the observation object, the support such that the camera is moved to a position so as to obtain a working distance between the camera and the observation object that is set for the special-light observation mode and that is shorter than a working distance between the camera and the observation object in the normal observation mode,
calculating a zoom magnification to obtain a field of view identical to a field of view in the normal observation mode with regard to a working distance between the camera and the observation object corresponding to the special-light observation mode; and
moving the camera to a position to obtain the working distance between the camera and the observation object corresponding to the special-light observation mode and change a magnification of the zoom lens to the calculated zoom magnification.

* * * * *